(12) United States Patent
Braun et al.

(10) Patent No.: US 10,092,005 B2
(45) Date of Patent: Oct. 9, 2018

(54) METHOD OF CONTROLLING WATER SURFACE INHABITING PESTS

(71) Applicant: SHA'KED MICROBIAL SOLUTIONS LTD., Tel Aviv (IL)

(72) Inventors: Sergei Braun, Zur-Hadassa (IL); Moshe Harel, Houston, TX (US)

(73) Assignee: SHA'KED MICROBIAL SOLUTIONS, LTD., Tel Aviv (IL)

( * ) Notice: Subject to any disclaimer, the term of this patent is extended or adjusted under 35 U.S.C. 154(b) by 0 days.

(21) Appl. No.: 14/899,965

(22) PCT Filed: Jul. 3, 2014

(86) PCT No.: PCT/IL2014/050602
§ 371 (c)(1),
(2) Date: Dec. 18, 2015

(87) PCT Pub. No.: WO2015/001563
PCT Pub. Date: Jan. 8, 2015

(65) Prior Publication Data
US 2016/0143290 A1     May 26, 2016

(30) Foreign Application Priority Data

Jul. 4, 2013   (IL) .......................................... 227343

(51) Int. Cl.
| *A01N 59/06* | (2006.01) |
| *A01N 59/00* | (2006.01) |
| *C02F 1/72* | (2006.01) |
| *A01N 43/66* | (2006.01) |
| *C02F 1/50* | (2006.01) |
| *C02F 1/68* | (2006.01) |
| *C02F 1/76* | (2006.01) |
| *C02F 103/00* | (2006.01) |

(52) U.S. Cl.
CPC ............ *A01N 59/06* (2013.01); *A01N 43/66* (2013.01); *A01N 59/00* (2013.01); *C02F 1/50* (2013.01); *C02F 1/72* (2013.01); *C02F 1/505* (2013.01); *C02F 1/687* (2013.01); *C02F 1/722* (2013.01); *C02F 1/76* (2013.01); *C02F 2103/007* (2013.01); *C02F 2303/04* (2013.01)

(58) Field of Classification Search
None
See application file for complete search history.

(56) References Cited

U.S. PATENT DOCUMENTS

| 3,761,238 | A | * | 9/1973 | Errede .................... A01N 25/08 504/151 |
| 4,692,335 | A | * | 9/1987 | Iwanski ................. A01N 25/34 252/187.24 |
| 2004/0185079 | A1 | * | 9/2004 | Zomer .................... A01N 25/12 424/405 |
| 2011/0079559 | A1 | | 4/2011 | Miller et al. | |

FOREIGN PATENT DOCUMENTS

| AU | 17587/92 | | 12/1992 | | |
| CN | 102351254 | | 2/2012 | | |
| JP | S5697206 | | 8/1981 | | |
| JP | S5738702 | | 3/1982 | | |
| JP | S62193698 | | 8/1987 | | |
| JP | H0368493 | | 3/1991 | | |
| JP | H103109990 | | 5/1991 | | |
| JP | H0667515 | | 8/1994 | | |
| JP | 2003113012 | | 4/2003 | | |
| JP | 2003261401 | | 9/2003 | | |
| JP | 2004107212 | | 4/2004 | | |
| JP | 2012116788 | * | 6/2012 | | |
| JP | 2012116788 | A * | 6/2012 | | |
| JP | 2012116788 | A * | 6/2012 | | |
| JP | 2013209326 | | 10/2013 | | |
| RU | 2113794 | | 6/1998 | | |
| RU | 23872 | | 7/2002 | | |
| RU | 2448051 | | 2/2012 | | |
| WO | 9220229 | | 11/1992 | | |
| WO | 1996003046 | | 2/1996 | | |
| WO | WO-9603046 | A1 * | 2/1996 | ............. | A01N 59/00 |
| WO | WO9603046 | A1 * | 2/1996 | | |
| WO | WO 9603046 | A1 * | 2/1996 | ............. | A01N 59/00 |

OTHER PUBLICATIONS

Arnette, Verna J., Cyanotoxin Removal in Drinking Water Treatment Processes, Dept. of Civil and Environmental Engineering, University of Cincinnati, Aug. 24, 2009, 118 pages.
Berg et al., High diversity of cultivable heterotrophic bacteria in association with cyanobacterial water blooms, The ISME Journal, Nov. 20, 2008, pp. 314-325. Wright State University, Advances in Botanical Research, vol. 27, pp. 211-256.
Chorus et al., Toxic Cyanobacteria in Water: A guide to their public health consequences, monitoring and management, 1999, pp. 1-36.
Esquenazi et al., Temporal dynamics of natural product biosynthesis in marine cyanobacteria, PNAS, Mar. 29, 2011, vol. 108, No. 13, pp. 5226-5231.
Falconer et al., Evidence of liver damage by toxin from a bloom of the blue-green alga, Microcystis aeruginosa, The Medical Journal of Australia, Aug. 1983, pp. 511-514.
Fallon et al., Lytic Organisms and Photooxidative Effects: Influence on Blue-Green Algae (Cyanobacteria) in Lake Mendota, Wisconsin, Applied and Environmental Microbiology, vol. 38, No. 3, Sep. 11979, pp. 499-505.
Haughey et al., Forms and fate of Cu in a source drinking water reservoir following CuSO4 Treatment, Water Res., vol. 34, No. 13, Jul. 1, 1999, pp. 3440-3452.
Hitzfeld et al., Cyanobacterial Toxins: Removal during drinking water treatment, and human risk assessment, Environmental Health Perspectives, vol. 108, Supplement 1, Mar. 2000, pp. 113-122.

(Continued)

*Primary Examiner* — Robert A Wax
*Assistant Examiner* — Quanglong Truong
(74) *Attorney, Agent, or Firm* — The Roy Gross Law Firm, LLC; Roy Gross

(57) ABSTRACT

The present invention discloses a method for controlling surface-inhabiting pests in an aquatic system, in particular cyanobacteria and harmful algal blooms (HABs), comprising spreading on the surface of the aquatic system a buoyant composition comprising a water disinfectant, preferably an oxidizing compound, and a floating agent. The invention further relates to compositions and methods for their preparation and use.

22 Claims, 6 Drawing Sheets

(56) References Cited

OTHER PUBLICATIONS

Carmichael, W. W., The Cyanotoxins, Dept. of Biological Sciences,
Jochimsen et al., Liver failure and Death After Exposure to Microcystins at a Hemodialysis Center in Brazil, The New England Journal of Medicine, vol. 338, No. 13, pp. 873-878.
Jones et al., Microbial diversity of soda lakes, Extremophiles, Feb. 16, 1998, pp. 191-200.
Kaplan et al., The languages spoken in the water body (or the biological role of cyanobacterial toxins), Frontiers in Microbiology, vol. 3, Article 138, Apr. 18, 2012, pp. 1-11.
Kolmakov, Methods for Prevention of Mass Development of the Cyanobacterium Microcystis aeruginosa Kutz emend. Elenk. in Aquatic Systems, Microbiology, vol. 75, No. 2, May 17, 2005, pp. 149-153.
Lamche et al., Recommended Chlorination Procedures for Receptacles Containing Mosquito Eggs for Quarantine Purposes, Bulletin of the Mosquito Control Association of Australia, vol. 14, No. 3, Nov. 2002, pp. 14-18.
Newman et al., Control of Microcystis aeruginosa by Decomposing Barley Straw, J. Aquat. Plant Manage, vol. 31, 1993, pp. 203-206.
Phelan et al., Microbial metabolic exchange—the chemotypeto-phenotype link, Nature Chemical Biology, vol. 8, Jan. 2012, pp. 26-35.
Sevilla et al., Iron availability affects mcyD expression and microcystin-LR synthesis in Microcystis aeruginosa PCC7806, Environmental Microbiology, 2008, vol. 10(10), pp. 2476-2483.
Shilo, Formation and Mode of Action of Algal Toxins, Bacteriological Reviews, vol. 31, No. 3, Sep. 1967, pp. 180-193.
Sigee, Biodiversity and Dynamic Interactions of Microorganisms in the Aquatic Environment, Freshwater Microbiology, University of Manchester, 2005, pp. 1-537.
Van Hullebusch et al., Environmental impact of two successive chemical treatments in a small shallow eutrophied lake: Part I. Case of aluminium sulphate, Environmental Pollution, vol. 120, 2002, pp. 617-626.
World Health Organization, Guidelines for Drinking-Water Quality, 2nd edition, vol. 2, Health criteria and Other Supporting Information—Addendum, 1998, pp. 1-127.
World Health Organization, Cyanobacterial toxins: Microcystin-LR in Drinking-water, Background document for development of WHO Guidelines for Drinking-water Quality, 1998, pp. 1-18.
Zohary et al., Hyperscums and the population dynamics of Microcystis aeruginosa, Journal of Plankton Research, vol. 12, No. 2, 1990, pp. 423-432.
Syrkina I. G. et al., Disinfectants, Chlorine Industry Series: an overview, Scientific Research Institute of Technical and Economic Research in the Chemical Complex, 1986, pp. 68-70, table 15.

\* cited by examiner

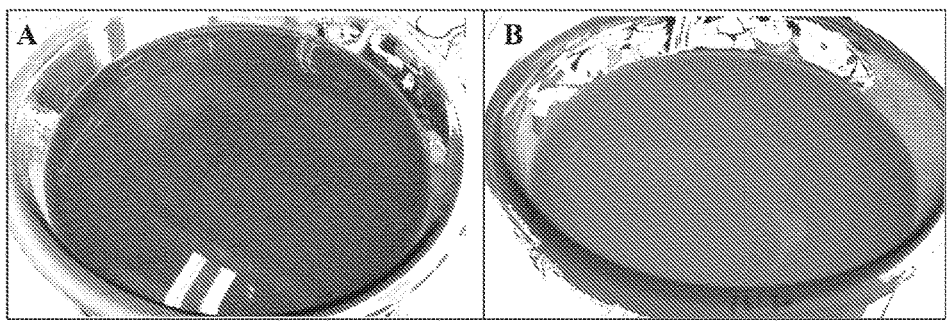
Fig. 1A                Fig. 1B
Fig. 2A        Fig. 2B        Fig. 2C        Fig. 2D
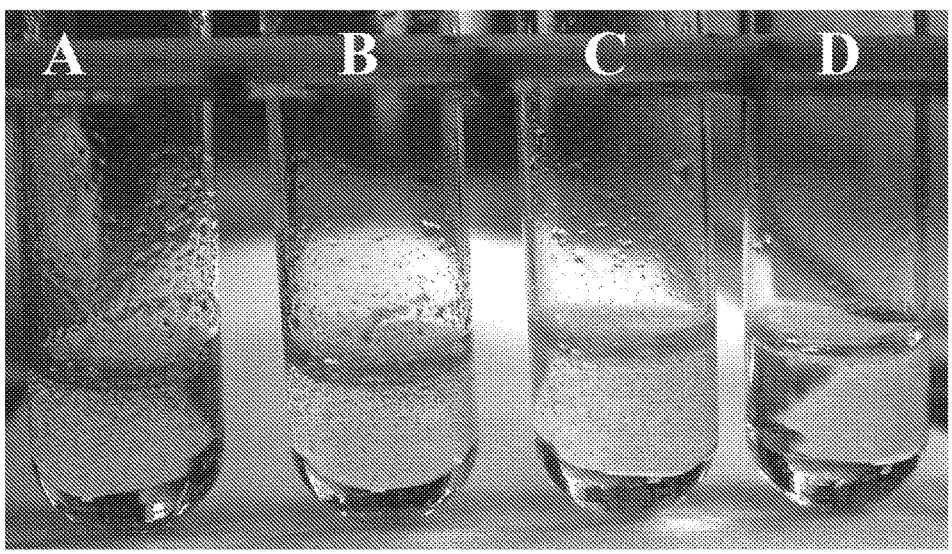

METHOD OF CONTROLLING WATER SURFACE INHABITING PESTS

TECHNOLOGICAL FIELD

The present invention is in the field of water disinfection.

PRIOR ART

References considered to be relevant as background to the presently disclosed subject matter are listed below:

Berg, K. A., Lyra, C., Sivonen, K., Paulin, L., Suomalainen, S., Tuomi, P., and Rapala, J. (2008) High diversity of cultivable heterotrophic bacteria in association with cyanobacterial water blooms. *ISME J* 3: 314-325.

Broza, M. and Halpern, M. (2001) Chironomid egg masses and *Vibrio cholerae*. *Nature* 412: 40.

Deng L. and Hayes P. K. (2008) Evidence for cyanophages active against bloom-forming fresh water cyanobactera. *Fresh Water Biology* 53: 1240-1252.

Di Domenico, D., Ruggeri, L., and Trentini, M. (2006) The use of sodium hypochlorite as ovicide against *Aedes albopictus*. *Journal of the American Mosquito Control Association* 22: 346-348.

Drabkova, M., Marsalek, B., and Admiraal, W. (2007) Photodynamic therapy against cyanobacteria. *Environ Toxicol* 22: 112-115.

Eiler, A. and Bertilsson, S. (2004) Composition of freshwater bacterial communities associated with cyanobacterial blooms in four Swedish lakes. *Environmental Microbiology* 6: 1228-1243.

Falconer, I. R., Beresford, A. M., and Runnegar, M. T. (1983) Evidence of liver damage by toxin from a bloom of the blue-green alga, *Microcystis aeruginosa*. *The Medical Journal of Australia* 1: 511.

Gardes, A., Iversen, M. H., Grossart, H. P., Passow, U., and Ullrich, M. S. (2010) Diatom-associated bacteria are required for aggregation of *Thalassiosira weissflogii*. *ISME J*

Hatchett, S. P. (1946) Chlorine as a possible ovicide for *Aedes aegypti* eggs. *Public Health Reports* (1896-1970) 61: 683-685.

Hullebusch, E. V., Deluchat, V., Chazal, P. M., and Baudu, M. (2002) Environmental impact of two successive chemical treatments in a small shallow eutrophied lake: Part II. Case of copper sulfate. *Environmental Pollution* 120: 627-634.

Iredale, R. S., McDonald, A. T., and Adams, D. G. (2012) A series of experiments aimed at clarifying the mode of action of barley straw in cyanobacterial growth control. *Water Research* 46: 6095-6103.

Jacups, S. P., Ball, T. S., Paton, C. J., Johnson, P. H., and Ritchie, S. A. (2013) Operational use of household bleach to "crash and release" *Aedes aegypti* prior to *Wolbachia*-infected mosquito release. *Journal of Medical Entomology* 50: 344-351.

Jones, B. E., Grant, W. D., Duckworth, A. W., and Owenson, G. G. (1998) Microbial diversity of soda lakes. *Extremophiles* 2: 191-200.

Kaplan, A., Harel, M., Kaplan-Levy, R. N., Hadas, O., Sukenik, A., and Dittmann, E. (2012) The languages spoken in the water body (or the biological role of cyanobacterial toxins). *Frontiers in Microbiology* 3.

Kolmakov, V. I. (2006) Methods for prevention of mass development of the cyanobacterium *Microcystis aeruginosa* Kutz emend. Elenk. in aquatic systems. *Microbiology* 75: 115-118.

Matthijs H. C. P., Visser P. M., Reeze B., Meeuse J., Slot P. C., Wijn G., Talens R., Huisman J. (2012) Selective suppression of harmful cyanobacteria in an entire lake with hydrogen peroxide. *Water Research* 46: 1460-1472.

Sigee, D. (2005) Biodiversity and Dynamic Interactions of Microorganisms in the Aquatic Environment. In *Freshwater Microbiology*. Chichester, UK: John Wiley & Sons, pp. 328-338.

Swaen, G. M., van Vliet, C., Slangen, J. J., and Sturmans, F. (1992) Cancer mortality among licensed herbicide applicators. *Scandinavian journal of work, environment & health* 18: 201-204.

Xiao, X., Huang, H., Ge, Z., Rounge, T. B., Shi, J., Xu, X. et al. (2014) A pair of chiral flavonolignans as novel anti-cyanobacterial allelochemicals derived from barley straw (*Hordeum vulgare*): characterization and comparison of their anti-cyanobacterial activities. *Environmental Microbiology* 16: 1238-1251.

Acknowledgement of the above references herein is not to be inferred as meaning that these are in any way relevant to the patentability of the presently disclosed subject matter.

BACKGROUND

Photosynthetic microorganisms tend to form seasonal blooms in water bodies such as ponds, lakes, wastewater reservoirs and oceans. These blooms are defined by a massive increase in cell-number that can reach to up to $10^6$-$10^7$ cells/ml and over than 50 µg/l chlorophyll-a. The phenomenon can be apparent to naked eye when water turns dark-green, red or brown. Although the bloom consists mainly of microorganisms capable to convert light energy via photosynthesis, it also coexists with a variety of many other microorganisms that support the entire community (Gardes et al., 2010). In some cases due to biotic and abiotic conditions, some of the species, namely blue-green algae, better known as cyanobacteria, use their gas vesicles to position themselves on water surface to form biofilms (also described as scums or mats). Cyanobacteria are a diverse group of oxygenic photosynthetic prokaryotes that possesses a versatile physiological and wide ecological tolerance, which contributes to their competitive success over a broad spectrum of environments. For more than 40 years the abundance of these organisms intensified globally in lakes, reservoirs, rivers and brackish water environments. Their blooms produce a musty odor and, more seriously, toxins. Cyanobacterial harmful algal blooms (CHABs) indicate an alert situation to water authorities, environmental and health agencies, as they reflect eutrophication problems as well as secretion of a huge array of metabolites, some of them most toxic to eukaryotes (Kaplan et al., 2012).

Several means for treating algal blooms are presently employed, e.g. a sequential treatment with aluminum sulfate ($Al_2(SO_4)_3$) and copper sulfate (Hullebusch et al. 2002), peroxides (Drabkova et al., 2007), or herbicides (i.e. diuron, simazine, atrazine). However, these treatments are associated with grave environmental consequences (Falconer et al., 1983; Kolmakov, 2006; Swaen et al., 1992), and are also expensive (treatment with $Al_2(SO_4)_3$ is estimated at US$750,000 to US$1,000,000 per sq km).

Accordingly, the available treatments are mostly used in artificial small ponds, pools and small shallow lakes where the ecological aspect of overdosing is not crucial. These treatments are not adequate for large water bodies, nor are they suitable for repeated use due to toxicity and ecological impact, their relatively high cost and the requirement for very large inputs for their uniform dispersal.

Another means for preventing CHABs is dumping barley or rice straw into aquatic ecosystems, though the effect was not consistent (Iredale et al., 2012). A recent discovery of their active compounds (flavonolignans salcolin A and B) (Xiao et al., 2014) demonstrated their lytic efficacy over *Microcystis aeruginosa*. However, these active compounds are not commercially available and are yet to obtain the required environmental and regulatory clearances.

Cyanophages, lytic viruses that specifically attack cyanobacteria, were hypothetically suggested, but were never practically identified or used (Deng and Hayess, 2008).

Matthijs et al., (2012) used a dispersal device and treated the whole volume of a shallow 0.12 sq km lake with ~60 µM liquid $H_2O_2$. The procedure was expensive due to the high cost of the device, time consuming and risky due to the use of liquid hydrogen peroxide. Also, the chemical was recorded in the water two days post treatment. Moreover, frequent exposure to $H_2O_2$ in large scale areas and at high frequencies may induce cyanobacterial resistance to the compound in the long run.

Chironomids (Diptera; Chironomidae; *Chironomus*) are the most abundant species of insects in freshwater worldwide. They undergo a complete metamorphosis in four life stages; three are aquatic (eggs, larvae, pupae) and the last is the terrestrial adult stage. Females lay egg-masses (of 400-1,000 eggs) embedded in a thick gelatinous matrix on the edge of water bodies.

The Chironomids (also known as non-biting midges) cause severe ecological and economical nuisance. Massive swarms of adult Chironomids emerging from aquatic habitats near, or in urban areas affect tourism and real estate value and are associated with human allergic reactions. As larvae they clog water pipes and may reach the water supply systems of home-users ("red worms"). Furthermore, Chironomids' gelatinous egg-mass is reported to serve as a natural reservoir of *Vibrio cholera* (Broza and Halpern (2001)). Currently, the efforts to prevent cholera rely on a combination of sanitary hygienic measures. Pesticides, which are used against the chironomids' larvae, have limited success since in a chronic use, the midges were found to adjust and become resistant. Moreover, pesticides have a broad specificity and may harm the environment, including humans.

SUMMARY OF THE INVENTION

The present invention is based on the surprising finding that buoyant formulations of various bleaching agents are effective in reducing cyanobacterial population in treated water. Furthermore, the formulations have shown efficacy as ovicides of marine insects, dramatically reducing the number of healthy larvae hatching from the eggs.

Accordingly, the present invention provides in a first of its aspects a method for controlling surface-inhabiting pests in an aquatic system, the method comprising:
a. Obtaining a composition comprising at least one water disinfectant being an active agent releasing compound and at least one floating agent; and
b. treating the aquatic system with the composition under conditions that cause reduction, inhibition or elimination of said pest growth in the aquatic system.

In one embodiment, said at least one water disinfectant is an oxidizing water disinfectant.

In one embodiment, the at least one water disinfectant is selected from the group consisting of a chlorine releasing agent, a bromine-releasing agent, a peroxide-based compound, a copper salt, an aluminum salt, and any combination thereof.

In a specific embodiment, the water disinfectant is Calcium hypochlorite ($Ca(OCl)_2$) or Sodium dichloroisocyanurate (NaDCC).

In one embodiment, the floating agent is selected from the group consisting of cellulose derivatives, ground plant biomass, saturated hydrocarbons, resinous materials, foam, and natural or synthetic latex.

In a specific embodiment, the floating agent is wood dust.

In another specific embodiment, the floating agent is paraffin.

In another specific embodiment, the floating agent is rosin.

In another specific embodiment, the floating agent is extruded or expanded polystyrene foam.

In another specific embodiment, the floating agent is silicone foam.

In certain embodiments, the amount of the at least one water disinfectant is about 10% weight/weight (w/w), or about 20% w/w, or about 30% w/w, or about 40% w/w, or about 50% w/w or higher of the composition.

In certain embodiments, the composition is in the form of particles, granules, flakes, powder, pellets, pills, solution or a combination thereof.

In one embodiment, said pest growth is selected from the group consisting of cyanobacterial growth, algal growth, microbial growth, plankton growth, and water surface inhabiting insects.

In one embodiment, the treating step follows detection of a harmful algal bloom in the aquatic system.

In a specific embodiment, the treating is performed at the beginning of the bloom episode.

In another embodiment, the treating step is performed upon detection of said pest growth.

In a specific embodiment, said pest is cyanobacteria and said water disinfectant is administered at a concentration of between about 0.005 $g/m^2$ and about 50 $g/m^2$, or between about 0.5 ppm and about 50 ppm of the active agent.

In one embodiment, said treatment results in trace amounts of the active compound as measured in the water 0.5 hour, 1 hour, 2 hours, 3 hours, 24 hours or more after each treatment.

In a specific embodiment, said trace amounts of the active compound do not exceed 3 ppm, as measured 24 hours or more after each treatment.

In another embodiment, said pest is water surface inhabiting insects and said disinfectant is administered at a concentration of between about 50 ppm and about 1000 ppm.

In a specific embodiment, said surface inhabiting insects are *Culex* sp., *Aedes* sp., *Anopheles* sp. or Chironomidae sp.s.

In certain embodiments, said disinfectant acts as an ovicide.

In one embodiment, said treating step comprises single, dual or multiple administrations of the water disinfectant.

In certain embodiments, the treating step is performed three times a day, or twice a day, or once a day, or once a week, or once every two weeks, or once every three weeks, or once a month or at longer intervals.

In a specific embodiment, the treating step is performed once a day or twice a day for a period of 1 day, 2 days, 3 days, 4 days, 5 days or more.

In one embodiment, the dual or multiple administrations are with the same or with different disinfectants.

In certain embodiments, the treatment is performed by manual or mechanical dusters or by spreading a liquid solution, e.g. from a boat or a plane.

In another aspect, the present invention provides a composition for use in controlling surface-inhabiting pests in an aquatic system, the composition comprising at least one water disinfectant being an active agent releasing compound and at least one floating agent.

In one embodiment, said at least one water disinfectant is an oxidizing water disinfectant.

In one embodiment, the at least one water disinfectant is selected from the group consisting of a chlorine releasing agent, a bromine-releasing agent, a peroxide-based compound, a copper salt, an aluminum salt, and any combination thereof.

In a specific embodiment, the water disinfectant is Calcium hypochlorite or NaDCC.

In one embodiment, the floating agent is selected from the group consisting of cellulose derivatives, ground plant biomass, saturated hydrocarbons, resinous materials, foam, and natural or synthetic latex.

In a specific embodiment, the floating agent is wood dust.

In another specific embodiment, the floating agent is paraffin.

In another specific embodiment, the floating agent is rosin.

In another specific embodiment, the floating agent is extruded or expanded polystyrene foam.

In another specific embodiment, the floating agent is silicone foam.

In certain embodiments, the amount of the at least one water disinfectant is about 10% w/w, or about 20% w/w, or about 30% w/w, or about 40% w/w, or about 50% w/w or higher of the total composition.

In certain embodiments, the composition is in the form of particles, granules, flakes, powder, pellets, pills or a solution.

In one embodiment, said pest growth is selected from the group consisting of cyanobacterial growth, algal growth, microbial growth, plankton growth, and water surface inhabiting insects.

In one embodiment, the composition is administered following detection of a harmful algal bloom in the aquatic system.

In a specific embodiment, the composition is administered at the beginning of the bloom episode.

In another embodiment, the treating is performed upon detection of said pest growth.

In a specific embodiment, said pest is cyanobacteria and said at least one water disinfectant is administered at a concentration of between about 0.005 g/m$^2$ and about 50 g/m$^2$ or between about 0.5 ppm and about 50 ppm of the active agent.

In one embodiment, administration of said composition to the aquatic system results in trace amounts of the active compound as measured in the water 0.5 hour, 1 hour, 2 hours, 3 hours or more after each treatment.

In a specific embodiment, said trace amounts of the active compound do not exceed 3 ppm, as measured 24 hours or more after each treatment.

In another embodiment, said pest is water surface inhabiting insects and said at least one water disinfectant is administered at a concentration of between about 50 ppm and about 1000 ppm.

In a specific embodiment, said surface inhabiting insects are *Culex* sp., *Anopheles* sp. or Chironomidae sp.s.

In certain embodiments, said disinfectant acts as an ovicide.

In one embodiment, said composition is administered to the aquatic system once, twice, or more.

In certain embodiments, the composition is administered three times a day, or twice a day, or once a day, or once a week, or once every two weeks, or once every three weeks, or once a month or at longer intervals.

In a specific embodiment, the composition is administered once a day or twice a day for a period of 1 day, 2 days, 3 days, 4 days, 5 days or more.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 1 shows images of a glass jar filled with CHABs; (A) prior to treatment, (B) after overnight treatment with a buoyant formulation of Calcium hypochlorite.

FIG. 2 shows images of glass jars filled with CHABs and treated with various concentrations of Calcium hypochlorite; (A) no treatment, (B) 0.5 g/sq m of the Ca(OCl)$_2$, (C) 1.0 g/sq m, (D) 5.0 g/sq m.

DETAILED DESCRIPTION OF EMBODIMENTS

Figure 3A:
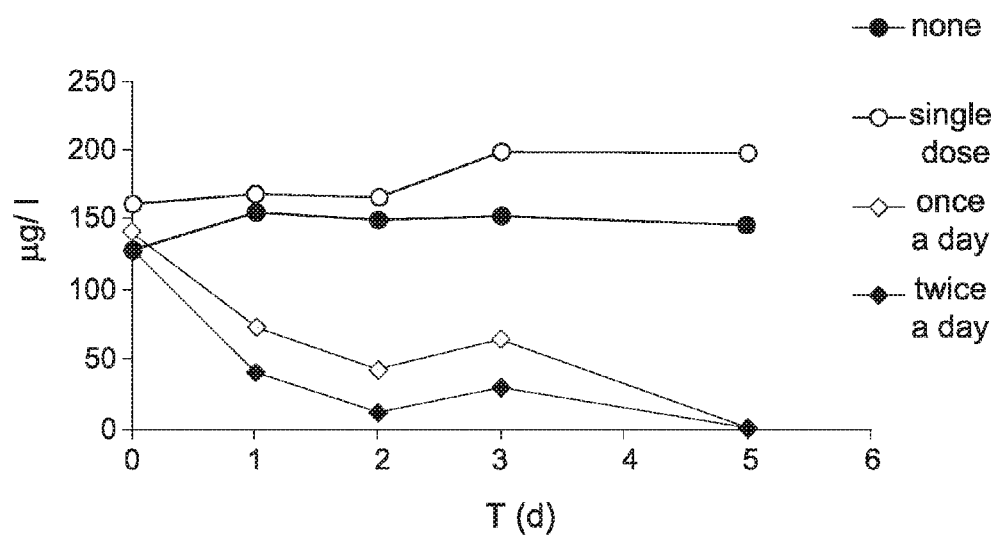
FIG. 3A is a graph of chlorophyll-a concentration (μg/l) at the water surface as a function of time (days).

The present invention relates to floating compositions comprising bleaching compounds (or oxidizers), suitable for the control of water surface inhabiting pests.

In particular, the present invention relates to a buoyant diffusible formulation containing Calcium hypochlorite, Sodium dichloroisocyanurate (NaDCC) or Sodium percarbonate (or other algaecides acting upon contact) suitable for the control of pests inhabiting water surface including first and foremost, cyanobacteria harmful algal blooms (CHABs) and surface inhabiting insects, as well as to methods for preparing the same.

The invention is based in part on the surprising finding that a floating formulation of Calcium hypochlorite or NaDCC demonstrated excellent efficacy against massive mats of cyanobacteria, at 'total Cl concentration' (the total Cl concentration within a water column) which is much lower than the level of chlorine permitted in potable water.

Hypochlorite and other oxidizers have been used for decades as purifying agents in drinking water supply systems Similarly, small bodies of water such as swimming and recreational pools are often purified against algae and bacteria by systematically treating them with hypochlorite in high concentrations. This solution is obviously not suitable for large basins such as lakes or open water bayous due to high costs related with large quantities of the compound needed, nonspecific lethal effects of bleach on the entire ecosystem's fauna and flora.

The present invention is based on the realization that ill effects of using a water disinfectant acting on contact could be remedied by lowering the actual concentration of the compound in the water column This is achieved by maintaining a gradient of the disinfectant (e.g. hypochlorite or hydrogen peroxide) in the column of water by slow release of the compound from a diffusible buoyant formulation. The concentration gradient of the disinfectant is produced by diffusion of the compound in water and optionally also by its rapid interaction with organic material in the water (including with the phytoplankton). The water surface is where the mass of cyanobacteria is situated as mats, and hence, applying the floating composition of the invention at the water surface can hold back a potential algal toxic bloom outbreak.

The novel treatment concept stems from the surprising finding that relatively small amounts of the oxidizing compound are sufficient for triggering an overwhelming reaction by the phytoplankton and especially cyanobacteria populations. This effect could be achieved by using a floating formulation of the oxidizing compounds. When repeated at a certain frequency (according to the initial cyanobacteria content and composition, as well as the overall load of the organic material in the water) the cyanobacterial cell numbers begin to decline, eventually leading to the collapse of the HAB population and optionally to the colonization of the water column by competing non-harmful organisms. This method enables a simple treatment with very low input requirements for dispersal of the oxidizers and facilitates economical usage of mass dispersal methods (e.g. boats and crop dusting planes). Moreover, due to the low dosage of oxidizers and due to the massive organic load in the treated water, the total available oxidizing-agent concentration in the water is significantly lower than the concentration allowed by regulators in treated drinking water (1-3 ppm of available chlorine) providing a safe and simple treatment with minimal adverse environmental effects.

Without wishing to be bound by theory, hypochlorite reacts in the column of water with abundant organic matter at the surface, and thus does not accumulate in the water column. Every molecule of chlorine reacts with organic matter that is present in the aquatic system and therefore the concentration of available or total-chlorine is almost non-detectable after a very short time.

The method of the present invention provides a simple and non-expensive solution compared to current treatments using Aluminum Sulfate. The solution provided by the present invention is about 15-20 times cheaper than the current $Al_2(SO_4)_3$ treatment, significantly more effective as well as significantly less toxic to the environment.

As a result of the treatment the algal and cyanobacterial numbers can be significantly reduced. As a consequence, the release of toxins, which is typically associated with the lysis of cyanobacteria cells at the end of the season, can either be avoided or significantly reduced, thus avoiding the detrimental effects of CHABs on water quality, while avoiding widespread harm to water-inhabiting organisms.

Therefore, the present invention provides a method for controlling surface-inhabiting pests in an aquatic system; the method comprising:
(a) Obtaining a composition comprising at least one water disinfectant being an active agent releasing compound and at least one floating agent; and
(b) treating the aquatic system with the composition under conditions that result in reduction, inhibition or elimination of said pests in the aquatic system.

As used herein the term "controlling surface-inhabiting pests" relates to the reduction, inhibition, prevention of accumulation, or elimination of said pest growth in the aquatic system.

As used herein the term "pest" encompasses microorganisms and organisms inhabiting water surfaces including but not limited to algae (e.g. cyanobacterial harmful algal blooms (CHABs), and organisms causing phenomena such as red tides (caused by dinoflagellates) or sea foam, bacteria, plankton, phytoplankton water surface inhabiting insects (i.e., adult subjects, eggs or larvae of biting flies, Chironomidae (Tanypodinae) or Culicidae, e.g. *Culex quinquefasciatus* or *Anopheles stevensi*). Therefore, non limiting examples of water surface inhabiting insects include *Culex* sp., *Aedes* sp., *Anopheles* sp. and Chironomidae sp.

In a specific embodiment, the pest is cyanobacteria and cyanobacterial harmful algal blooms (CHABs).

As used herein the term "algal bloom" relates to a rapid increase or accumulation in the population of algae (typically microscopic) in an aquatic system. Algal blooms may occur in freshwater as well as marine environments, and are also referred to as scum or floating algal mats. The term "harmful algal bloom" (HAB) relates to an algal (or cyanobacterial) bloom that causes negative impacts to other organisms via production of toxins, mechanical damage to other organisms, or by other means. The term encompasses any macro- or micro-photosynthetic organisms including green algae as well as cyanobacteria such as (but not limited to) *Microcystis, Anabaena, Planktothria, Nostoc, Nodularia, Oscillatoria* sp., *Cylindrosperum, Planktothrix* spp., *Aphanizomenon* spp., *Lyngbya* and species such as *Anabaena flos-aquae* and *A. planktonica* as well as marine dinoflagelates, which are associated with the red-tides within the harmful marine algal blooms.

The composition of the invention, and in a specific embodiment, a composition comprising hypochlorite or hydrogen peroxide, would not only affect the algal bloom but also commensal bacterial species, which are associated with the CHABs. It is known that different bacterial species have a major role in the existence of the CHABs (Eiler and Bertilsson, 2004; Jones et al., 1998; Sigee, 2005). Some of them cause, independently, adverse health effects for humans and animals (Berg et at, 2008).

Moreover, the compositions of the invention, and in particular compositions comprising hypochlorite or hydrogen peroxide, also have an indirect detrimental effect on insects. In particular, insects which inhabit the water-surface interface, at least at a portion of their life cycle, for example, but not limited to, Chironomids, *Anopheles* and others.

In certain aspects the methods of the present invention target the non-motile eggs of the insects. 250-500 ppm of concentrated hypochlorite caused 95% of egg populations not to hatch. Other eggs hatched prematurely and most of the hatched larvae did not mature into adults.

Without wishing to be bound by theory, elimination of the egg-masses from the environment would not only affect chironomid population, but may also diminish *V. cholerae's* ability to spread in water or to be consumed and therefore transmitted to humans.

As used herein the term "aquatic system" encompasses natural or artificial systems such as lakes, rivers, fountains, ponds (e.g. fish ponds), canals, aquariums, aquaculture systems, water holding or conveying systems, water reservoirs, open drinking water systems, brackish water environments, waste water and oceans.

As used herein the term "water disinfectant" relates to a compound capable of removal, deactivation or killing of microorganisms in water.

In preferred embodiments the water disinfectant is an active agent releasing compound. In another embodiment the water disinfectant is an oxidizing water disinfectant.

Non limiting examples of water disinfectants in accordance with the invention include: chlorine based compounds (also referred to as "chlorine releasing agents") (e.g. hypochlorite (OCl), Calcium hypochlorite, Sodium hypochlorite, sodium dichloroisocyanurate (NaDCC, dehydrate monohydrate or anhydrous), dichloro-diphenyl-trichloroethane (DDT)) copper sulfate, bromine based compounds (also referred to as "bromine-releasing agents"), iodine (I), Iodophores, Potassium permanganate ($KMnO_4$), and peroxide-generating compounds (e.g. hydrogen peroxide, sodium per-carbonate, calcium peroxide, solidified hydrogen peroxide-PVP complexes, sodium per-borate (tetrahydrate or monohydrate), Peracetic acid). Preferably, the water disinfectant is an oxidizing agent that reacts with water and with the organic material in the water thereby producing non-toxic products that do not accumulate or change the aquatic environment.

For example, suitable reactive chlorine- or bromine-containing, oxidizing agents include heterocyclic N-bromo and N-chloro imides such as trichloroisocyanuric, tribromoisocyanuric, dibromoisocyanuric and dichloroisocyanuric acids, and salts thereof with water-solubilizing cations such as potassium and sodium (e.g. Sodium dichloroisocyanurate (NaDCC) dehydrate or NaDCC anhydrous). Additional agents include Chloramine T (Sodium salt of N-chloro-4-methylbenzenesulfonamide), Dichloramine T (N,N-dichloro-4-methylbenzene-sulfonamide), or chlorine-releasing quaternary ammonium compounds (e.g. benzalkonium chloride, benzethonium chloride and cetylpyridinium chloride). Hydantoin compounds such as 1,3-dichloro-5,5-dimethyl-hydantoin are also suitable. Dry, particulate, water-soluble anhydrous inorganic salts are likewise suitable for use herein such as lithium, sodium or calcium hypochlorite and hypobromite, as well as chlorinated trisodium phosphate.

For example, suitable peroxide-based compounds include organic peroxy-acids. The peroxy-acids usable in the present invention are solid and, preferably, substantially water-insoluble compounds. In one embodiment typical monoperoxy acids useful herein include alkyl peroxy-acids and aryl peroxy-acids such as, peroxy-benzoic acid and ring-substituted peroxy-benzoic acids, e.g. peroxy-alpha-naphthoic acid or aliphatic and substituted aliphatic monoperoxy-acids, e.g. peroxy-lauric acid and peroxy-stearic acid.

Inorganic peroxygen-generating compounds may also be suitable as cores for the particles of the present invention. Examples of these materials are salts of monopersulphate, copper sulfate, perborate monohydrate, perborate tetrahydrate, and percarbonate.

In another embodiment, the water disinfectants are aldehydes (e.g. formaldehyde or glutaraldehyde) and solidified compounds thereof.

In one embodiment the composition of the invention comprises a mixture of any of the above listed compounds such as, but not limited to, Copper sulfate and any hypochlorite compound. Preferably such a mixture will result in a synergistic effect.

In one embodiment, the method of the invention comprises sequential administrations of the composition of the invention wherein in each administration a different water disinfectant is used.

The term "water disinfectant" also encompasses bleaching agents or compounds.

Non-limiting examples of active agents released by the active agent releasing compound are Chlorine ($Cl_2$), Chlorine dioxide ($ClO_2$), Ozone ($O_3$), halogens (e.g. bromine ($Br_2$), bromine chloride (BrCl), metals (e.g. copper ($Cu^{2+}$), silver ($Ag^+$), Alum, Phenols, alcohols, soaps and detergents.

In a specific embodiment, the water disinfectant is any compound suitable for water disinfection that produces hypochlorous acid or hydrogen peroxide as the active compound.

In specific embodiments said water disinfectant is Calcium hypochlorite, sodium dichloroisocyanurate (NaDCC) dihydrate, or Sodium percarbonate.

As used herein the term "floating agents" relates to compounds capable of floating on the surface of water. Non limiting examples of floating agents include cellulose derivatives, ground plant biomass, saturated hydrocarbons, resinous materials, foam, gelling agents and natural or synthetic latex.

In one embodiment the floating agent is wood dust (also termed sawdust). In a specific embodiment, the composition comprises sawdust and Calcium hypochlorite granules. The composition is prepared, for example, by adding Calcium hypochlorite granules (e.g. 14-50 mesh) to sawdust, the compounds are partially sealed with a silicone adhesive, thoroughly mixed and then crushed to the desired particle size.

In one embodiment the floating agent is paraffin. In a specific embodiment, the composition comprises Calcium hypochlorite and paraffin. The composition is prepared, for example, by mixing Calcium hypochlorite powder at a ratio of 1:2 w/w with paraffin at the melting point of paraffin and then either extruded or cooled and made into 3-4 mm flakes.

In one embodiment the floating agent is rosin. In a specific embodiment, the composition comprises Calcium hypochlorite and rosin. The composition is prepared, for example, by mixing Calcium hypochlorite powder at a ratio of 1:2 w/w with rosin at the melting point of rosin and then either extruded or cooled and made into 3-4 mm flakes.

The floating agent may be foam, for example any foam-former of suitable resistance to oxidation, e.g., Styrofoam or silicon foams.

Thus, in one embodiment the floating agent is extruded or expanded polystyrene foam. In a specific embodiment, the composition comprises Calcium hypochlorite and extruded or expanded polystyrene foam. The composition is prepared, for example, by mixing Calcium hypochlorite granules with the viscous polymer pre-foam solution and then curing.

In another embodiment the floating agent is silicone foam. In a specific embodiment, the composition comprises Calcium hypochlorite and silicone foam. The composition is prepared, for example, by mixing Calcium hypochlorite granules with the viscous polymer pre-foam solution and then curing.

In a specific embodiment the floating agent is an aqueous foam solution containing a foam-generating chemical capable of producing foam when mixed with gas, e.g. air.

In a specific embodiment the composition of the invention comprises an aqueous foam comprising chlorine dioxide. An aqueous solution comprising the disinfectant agent and capable of forming a foam is prepared for example by adding a foaming agent, i.e., a suitable surfactant, to water. Chlorine dioxide may then be added to the solution or it may be generated in-situ by reacting an oxidizing agent, or a cationic exchange resin in the acidic form, or an acid with a metal chlorite dissolved therein. The resultant foam solution may subsequently be foamed by being mixed with air in a foam generator.

In another embodiment the floating agent is a gelling agent, e.g. hydroxypropyl methylcellulose. In a specific embodiment, the composition comprises dichloroisocyanuric acid sodium salt dehydrate (NaDCC) and hydroxypropyl methylcellulose.

In certain embodiments the composition may further comprise at least one binding agent, e.g. Glyceryl Stearate. Without wishing to be bound by theory the addition of Glyceryl Stearate decreases friability of the pellets and increases the buoyancy.

In certain embodiments the composition may further comprise at least one swelling agent, e.g. sodium chlorite, Citric Acid or Sodium Bicarbonate.

Without wishing to be bound by theory, sodium bicarbonate and citric acid react and release carbon dioxide upon exposure to water and thereby further reduce the compound's dissolution time.

Thus in one specific embodiment the composition comprises NaDCC, hydroxypropyl methylcellulose, Glyceryl Stearate, and sodium chlorite or Citric Acid and Sodium Bicarbonate.

In another embodiment, the composition comprises Calcium hypochlorite coated with at least one layer of film-forming latex in a hydrocarbon. The density of the coated particles depends on the porosity of Calcium hypochlorite pellets and the character of the coating.

The amount of the at least one water disinfectant in the composition may range from about 10% w/w, or about 20% w/w, or about 30% w/w, or about 40% w/w, or about 50% w/w or higher of the total composition.

In certain embodiments the compositions may be prepared by mixing, compression, hardening, or coating so as to form solid particles.

In certain embodiments the composition is in the form of particles, flakes, powder, pills, pellets, or solution.

In one embodiment said treating step (b) is performed by dispersing the composition on the water surface. The dispersion may be performed by spraying the composition over the aquatic system, e.g. by creating aerosol.

In one embodiment, the treatment begins at the beginning of the bloom season optionally under a routine monitoring system.

In a specific embodiment, the composition is spread before, or at the onset of a bloom episode and prevents a potential toxic bloom outbreak. The treatment frequency can be daily, weekly or monthly—for example, in accordance with the organic load, variety of other phytoplankton and microorganism populations and type of the harmful microorganisms.

The treatment may be repeated for a few days, halted and then resumed if and when the cell numbers rise.

The algal mats are driven on the surface of water by the currents and winds. The floating formulation of the invention moves together with its target thus only the areas of accumulation of algae and not the whole surface of water should be treated.

The effective treatment protocol can be determined by a person skilled in the art according to the local conditions in the aquatic system. The treatment may be provided as a single dispersion or as multiple dispersions. The frequency of treatment may be determined according to the local conditions and may for example be three times a day, or twice a day, or once a day, or once a week, or once every two weeks, or once every three weeks, or once a month or at longer or shorter intervals. In one embodiment the treatment is performed once at the beginning of the season with the appearance of the cyanobacteria and repeated, if necessary.

Reduction, inhibition or elimination of algal growth can be easily determined using various methods. Non limiting examples include: visual detection, for example by inspecting the color and/or consistency of the water, analysis of genetic markers, e.g. the abundance of specific DNAs originating from these organisms such as those encoding for their ribosomes, measuring chlorophyll-a content, microscopic measurements of cyanobacterial cell numbers, measuring dissolved oxygen concentrations in the water, or by measuring the pH in the water, whereby an increase in pH is indicative of an increase in cyanobacterial cell numbers.

In one embodiment the total concentration of the oxidizing agent (e.g. Calcium hypochlorite or NaDCC) in the water of the aquatic system is significantly lower than the level of chlorine permitted in potable water, preferably, 0.003 mM to 0.03 mM, or 0.05-50 g/m$^2$ of the water surface or lower, or between about (0.5 ppm) and about (50 ppm) of the active agent.

For example (see Examples 1 and 2 below), the inventors demonstrated that application of as little as 5 g/m$^2$ at the surface of highly polluted water obtained from a small pond at the Jerusalem Zoo contaminated with more than 10$^9$ *Microcystis* cells/ml was sufficient for the total elimination of the algal mat. Taking for comparison the shallow Green lake (Seattle, USA) with a surface of 1.05·10$^6$ m$^2$ and a water volume of 4.12·10$^6$ m$^3$, only 5 ton of Ca(OCl)$_2$ of the buoyant formulation can be used as compared with 44 ton of the comparative non-buoyant formulation for the permitted range of hypochlorite in potable water.

Furthermore, application of as little as 1.2 or 1.6 g of NaDCC to enclosures having a volume of about 270 liter was sufficient for the total elimination of the cyanobacterial infestation (as shown in Examples 5 and 6 below).

The amount of dispersed oxidizers in accordance with the method of the invention depends on the amount of organic material in the water. Calcium hypochlorite or NaDCC interact with the organic material on contact and thereby their effective concentration is rapidly reduced. Namely, the active compound of the floating formulation interacts immediately with the organic load existing in the water without leaving any detectable residue and without accumulating in the environment.

The invention also provides a slow release floating formulation of a bleaching compound. Specifically, the invention provides a floating algal growth inhibitor, a floating water-borne insect-ovicide, or a floating composition comprising a compound that reduces insect oviposition on water.

Without wishing to be bound by theory, the present invention provides simple and cost-effective methods for interfering with the ecological niches of cyanobacteria or green algae (phytoplankton). This interference provides a temporary advantage to competitive microorganisms in the same environment and allows them to take over and successfully compete with the harmful phytoplankton. Namely, the methods of the invention are not aimed at completely eliminating the cyanobacteria or green algae from the water, as is the common practice with antibiotics, but to provide means for temporary changes in their ecological niche. Such an approach has never been used in large water basins.

In another embodiment, and in particular for the treatment of water inhabiting insects, eggs or larvae, the total concentration of the oxidizing agent (e.g. Calcium hypochlorite or NaDCC) is about 50 ppm, or 100 ppm, or 200 ppm or 250 ppm or 300 ppm, or 400 ppm, or 500 ppm, or 600 ppm, or 700 ppm, or 800pp, or 900 ppm, or 1000 ppm or more of the active agent. In one embodiment, the total concentration of the oxidizing agent is between about 50 ppm and about 1000 ppm of the active agent. Preferably, the total concentration of the oxidizing agent is between about 50 ppm and about 500 ppm of the active agent.

With respect to water inhabiting insects, bleaching was not suggested previously as a commercial ovicide, probably since high levels of the oxidizing agent could not be reached and sustained at the location of the eggs at the water surface (Di Domenico et al., 2006; Hatchett, 1946; Jacups et al., 2013).

As used herein the term "ovicide" relates to an agent that kills or damages insect eggs, thereby preventing their regular hatching and the development of the larvae into a grown subject.

As demonstrated in Example 5 below, the concentration of hypochlorous acid at natural environments disappears rapidly from the water (upon reaction with organic matter of any sort). Although these hypochlorous acid concentrations affected phytoplankton very efficiently—as shown in Example 5—they did not effectively affect mosquito eggs, or their larvae which escaped the active compound by swimming away. In contrast, the series of experiments presented in Example 7 demonstrates, on different types of water-borne insects, that a relatively high concentration of bleach (e.g. NaDCC) is required to destroy the insects' eggs. Since these insects' eggs are normally laid in large water bodies, treating them with a non-floating formulation would cause the bleach-load to dilute in the entire body of the water, thus failing to reach effective concentrations in order to affect the eggs or otherwise cause premature hatch of the insects' larvae. The floating formulation of the present invention thereby provides an effective solution, allowing administration of the high concentrations (e.g. 50-500 ppm) of the oxidizer required for effective treatment at the water surface and thereby generate the desired ovicidal effect.

In addition, the process of laying eggs by female mosquitoes has been investigated for decades. Without wishing to be bound by theory, the females can detect harmful environment before laying their eggs on water surface. Therefore, using floating, slow release formulations of bleaching agents is expected to significantly reduce the amount of laid eggs in those systems.

EXAMPLES

Example 1

Determination of Sensitivity of Cyanobacteria to Hypochlorite

A 4 liter glass jar (Ø=65 mm, H=1210 mm) was filled with CHABs freshly sampled from the Biblical Zoo of Jerusalem (FIG. 1A). The heavy algal population consisted mainly of *Microcystis* sp. The polluted water was treated overnight with a buoyant formulation of Calcium hypochlorite. The buoyant formulation was prepared by placing Calcium hypochlorite particles on a floating sheet of paper. The water gradually wetted the paper and the Calcium hypochlorite particles gradually dissolved into the glass jar interacting with the organic material and forming a concentration gradient in the water. After overnight treatment with the buoyant formulation containing 0.5 mg of Calcium hypochlorite per sq cm (FIG. 1B), the average concentration of hypochlorite in the jar was 0.03 mM, considerably below the permitted level (0.075 mM) in potable water. The surface algae were lysed. Eukaryotic algae at the bottom of the jar were not affected due to the low concentration of Calcium hypochlorite at the bottom of the jar. No smell of chlorine could be detected at any stage of the experiments.

Example 2

Testing Various Calcium Hypochlorite Concentrations

The experiment was conducted as shown above in Example 1 using various concentrations of Calcium hypochlorite. Different concentrations of $Ca(OCl)_2$ were added to a 4 liter glass jar as shown in FIG. 2: (A) no treatment, (B) 0.05 mg/sq cm of the $Ca(OCl)_2$, (C) 0.1 mg/sq cm, (D) 0.5mg/sq cm. At the end of the experiment 2 ml from the surface of each tank were transferred into a 10 ml vial and left for several minutes to settle. FIG. 2 demonstrates the effects of the various concentrations. Each of the tested concentrations reduced the amount of the algal population.

Example 3

Preparation of Floating Composition of NaDCC Anhydrous with Beeswax

NaDCC anhydrous (Sigma # 218928) was mixed extensively with 50° C. pre-heated beeswax 1:1 w/w. This resulted in the formation of fine NaDCC particles partially encapsulated by the wax that enable floating of the active ingredient on the water surface.

Example 4

Preparation of an Exemplary Floating Formulation Comprising NaDCC

The exemplary product formulation included the following components:
Active ingredient: Sodium Dichloroisocyanuric acid NaDCC dihydrate (obtained from Acros Chemical)—39.4% w/w of the total formula
Gelling agent: Hydroxypropyl methylcellulose (Methocel 40-202 PCG obtained from DOW Chemical)—42.4% w/w of the total formula
Binding agent: Glyceryl Stearate (obtained from Making Cosmetics)—10.2% w/w of the total formula
Swelling agents: NaCl (obtained from Sigma Aldrich)—8% w/w of the total formula.
Alternatively, Citric Acid (obtained from Sigma Aldrich) and Sodium Bicarbonate (obtained from Chem-IMPEX INT'L Inc.)—each 4% w/w of the total formula Preparation Procedure The product formulation was prepared as follows: NaCl, citric acid, and sodium dichloroisocyanuric acid (NaDCC) dehydrate were ground in separate containers thus achieving a particle size range of about 0.2 to 0.7 mm Alternatively, NaCl was replaced by glyceryl stearate and sodium bicarbonate. This creates particles that can be evenly distributed throughout the product. Next, Methocel 40-202 PCG, glyceryl stearate, dichloroisocyanuric acid sodium salt dihydrate, citric acid, and sodium bicarbonate were combined in a large container and stirred until all of the ingredients were well mixed. Once well mixed, the mixture was fed into a pellet press with a 12 mm diameter. The press was adjusted to create a pellet that is about 7 mm thick and has a mass of about 500 mg. The pellets were then incubated in a 115° C. oven for 3 minutes, removed from the oven and allowed to cool.

Dissolution Study

The ability of the pellet to release free available chlorine from the water soluble NaDCC was measured over time using a colorimetric method. Three pellets were selected at random from the kilogram batch that was created. The dimensions and mass of each pellet was recorded and the pellets were added to an 800 ml high density polyethylene (HDPE) beaker filled with deionized water and covered with aluminum foil. The dimensions and mass of the randomly selected pellets are reported in Table 1. NaDCC (0.1975 g) was added to a separate 800 ml plastic beaker as a control. 0.8 ml aliquots of each solution were pipetted into 50 ml volumetric flasks and brought to volume with deionized water. 10 ml aliquots of these diluted solutions were mixed with 100 µl of 0.1% orthotolidine in a vial, forming a clear, yellow solution. The solution was loaded into a cuvette and was analyzed using a Shimadzu UV160U UV-Vis Spectrophotometer at 436 nm.

TABLE 1

Dimension and Mass of the Randomly Selected Pellets

| A | 12 | 7 | 501.8 |
| B | 12 | 7 | 505.0 |
| C | 12 | 7 | 496.7 |

Initial sample pulls occurred 15 minutes after the pellets and control sample were added to the water. Additional pulls were taken at about 2, 9, 11, 13, 15, 17, 24, and 36 hours.

Upon exposure to water, NaDCC breaks down to release free available chlorine that acts as an algae growth inhibitor. Orthotolidine reacts with the chlorine causing a color change allowing for colorimetric analysis to chart the dissolution of the NaDCC. The concentration of NaDCC released at each time point was calculated by constructing a calibration curve relating the free available chlorine response to the initial concentration of NaDCC. The initial concentration of NaDCC calculation is shown in Equation 1. The original aliquot of the control taken at the 15 minute mark was used to create standards ranging from 25-250 ppm. The instrument response for each standard solution is shown in Table 2.

Concentration of initial NaDCC=initial mass of NaDCC/volume of deionized water     Equation 1

197.5 mg/0.800 L=246.9 ppm

TABLE 2

Standard Curve Concentration of NaDCC

| Concentration (ppm) | Response (AU) |
| --- | --- |
| 0.000 | 0.000 |
| 24.69 | 0.169 |
| 98.75 | 0.828 |
| 123.4 | 1.013 |
| 148.1 | 1.356 |
| 246.9 | 2.053 |

The concentration of NaDCC released by the pellets over time was calculated using the relationship found between concentration and response from the calibration curve, which is also shown in Equation 2. The response of each randomly selected pellet (labeled "A", "B", and "C") and the control standard are reported in Table 3. The response was converted to concentration in Table 3 using Equation 3.

Response (AU)=0.0085×Concentration (ppm)     Equation 2

Concentration (ppm)=Response (AU)/0.0085     Equation 3

TABLE 3

Response of the Randomly Selected Pellets and Control Standard over Time

| Time (hours) | Control | A | B | C |
| --- | --- | --- | --- | --- |
| 0.25 | 2.053 | 0.000 | 0.000 | 0.000 |
| 2.17 | 1.941 | 0.034 | 0.091 | 0.036 |
| 9.17 | 2.022 | 0.794 | 0.973 | 0.848 |
| 11.00 | 1.831 | 1.168 | 1.385 | 1.219 |
| 13.42 | 2.030 | 1.662 | 1.595 | 1.590 |
| 15.42 | 1.988 | 1.721 | 1.712 | 1.677 |
| 17.67 | 1.968 | 1.649 | 1.628 | 1.688 |
| 24.00 | 1.850 | 1.753 | 1.889 | 1.809 |
| 36.00 | 2.015 | 1.880 | 1.956 | 1.889 |

TABLE 4

Concentration (ppm) of NaDCC Released by the Randomly Selected Pellets and Control Standard over Time

| Time (hours) | Control | A | B | C |
| --- | --- | --- | --- | --- |
| 0.25 | 241.5 | 0.000 | 0.000 | 0.000 |
| 2.17 | 228.4 | 4.000 | 10.71 | 4.235 |
| 9.17 | 237.9 | 93.41 | 114.5 | 99.76 |
| 11.00 | 215.4 | 137.4 | 162.9 | 143.4 |
| 13.42 | 238.8 | 195.5 | 187.6 | 187.1 |
| 15.42 | 233.9 | 202.5 | 201.4 | 197.3 |
| 17.67 | 231.5 | 194.0 | 191.5 | 198.6 |
| 24.00 | 217.6 | 206.2 | 222.2 | 212.8 |
| 36.00 | 237.1 | 221.2 | 230.1 | 222.2 |

As shown above, the exemplified formulation floats and slowly releases NaDCC over time.

The release of NaDCC occurred at a relatively linear rate until 15 hours. After 15 hours, the rate of release slowed down dramatically. By 15 hours, about 85% of the NaDCC was released and by 24 hours about 90% was released.

Example 5

Use of the Floating Formulation to Reduce Cyanobacterial Cell Density [I]

Figure 3B:
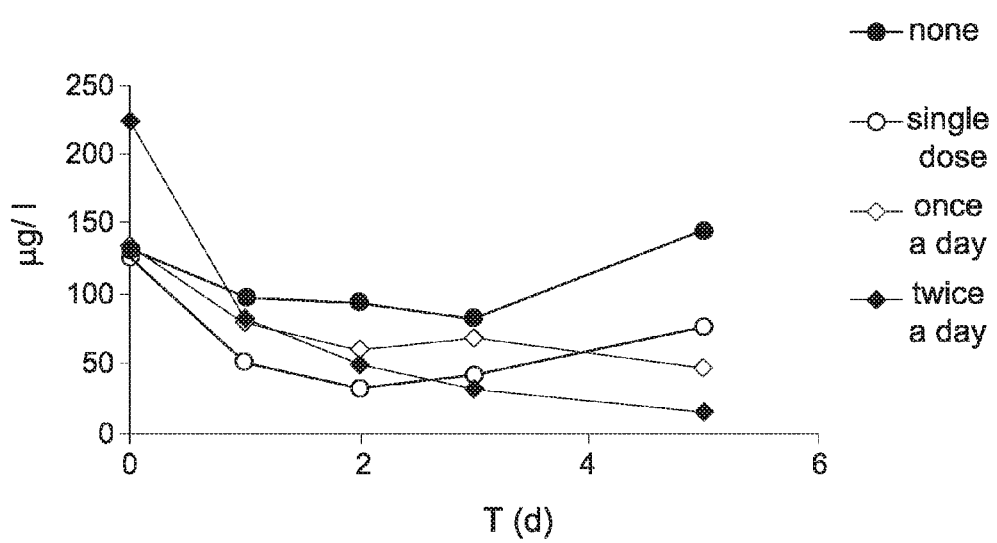
FIG. 3B is a graph of chlorophyll-a concentration (μg/l) in a depth of 50 cm as a function of time (days).
Figure 3C:
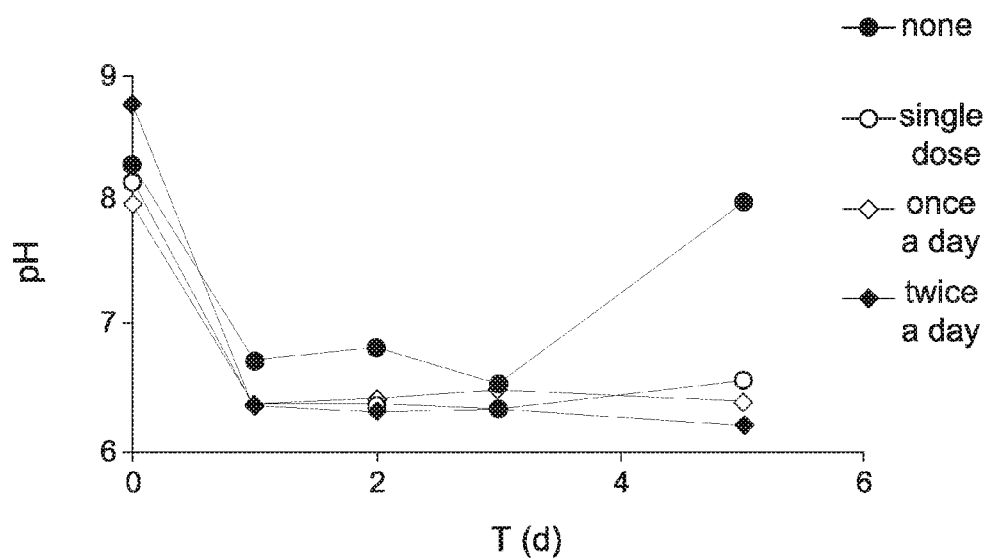
FIG. 3C is a graph of pH measurements as a function of time (days).
Figure 3D:
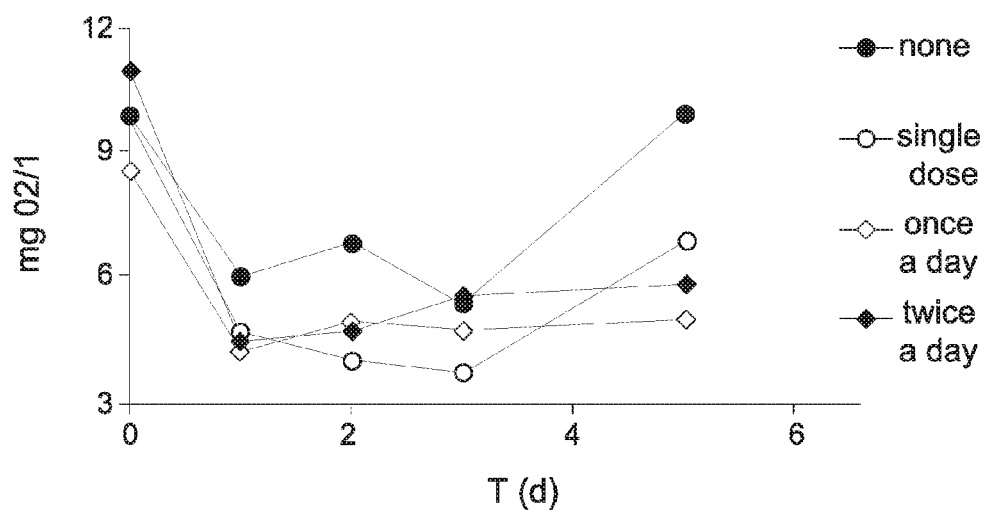
FIG. 3D is a graph of dissolved oxygen concentration (mgO$_2$/l) at the water surface, as a function of time (days).

Enclosures [2.0 m long polyethylene clear tubes with 20 cm radius (0.125 sq m) surface area] were set in an aerated fish pond (S10 pond, Auburn University, Auburn, Ala.) infested with the toxic cyanobacterium *Oscillatoria* sp. (as the predominant species) with a chlorophyll concentration of ~150 µg/l and microcystins levels of 0.2 µg/l. Three independent assays were set and were treated by capsules (pellets) containing ~200 mg sodium dichloroisocyanurate (NaDCC) dihydrate granules as an active ingredient. The capsules were prepared as demonstrated in Example 4. The enclosure was open to the pond's floor and was subjected to movement of the water by a forceful aerator that worked every morning on a daily basis for a few hours each time. Four different treatments were applied: 8 capsules (total of 1.6 g of NaDCC dehydrate) at (1) single dose at day 1 only; (2) one dose every morning for 5 days, (3) one dose twice a day for 5 days, and (4) no treatment. All enclosures were sampled three hours post morning treatment. Chlorophyll-a concentration was measured at water surface as well as at 50 cm depth. This reading is accepted as a direct indication for the phytoplankton cell density. Also, levels of dissolved oxygen (DO), pH (all depths), total suspended solids (TSS) at the surface, conductivity, and light extinction were taken. The following surprising findings were observed:

1. Three hours after the first treatment, a 50-70% decrease in chlorophyll-a concentration was observed on the water surface which reached 99.96% decrease over 5 days of treatment in the repetitive treatments (FIG. 3A). Unexpectedly, the repetitive treatment affected also the water column, as was observed at 50 cm depth with a decline of 50%-99% chlorophyll-a in comparison to time 0 and no treatment control (FIG. 3B).
2. The reduction in cyanobacterial numbers resulted also in a decrease of the photosynthesis yield: lower consumption of $CO_2$ from the system reduced carbonic acid and lead to a greater bicarbonate concentration and therefore reduction of the pH level. The pH decreased from 8.0 to 4.0 (FIG. 3C).
3. Dissolved oxygen (DO) measurements were also expected to decrease due to the loss of the photosynthesis yield: the concentration of $O_2$ in the water was reduced very fast, namely after one day $O_2$ concentrations were reduced by ~50% and lasted for the 5 days of measurements (FIG. 3D).
4. Light extinction as measured along the water column, as well as TSS or conductivity were surprisingly not altered, despite the significant reduction in phytoplankton.

Without wishing to be bound by theory, pH and DO readings clearly demonstrate that the cyanobacterial physiology was altered in the beginning of the treatment even before cyanobacterial cells started to disappear from the water. This hypothesis is supported by the lack of change in light extinction coefficient, conductivity and total suspended solids (TSS) readings. Moreover, the readings of these three parameters remained constant throughout the entire assay and consistent across all 3 blocks of the experiment, suggesting that other populations of microorganisms took over the ecological niche the moment the cyanobacteria diminished. Alternatively, the other populations of microorganisms may have predated on the nutritious cyanobacterial cell content.

Another support to that claim is that chlorine concentration was almost non detectable along the whole assay neither at the water column nor on the surface, and did not exceed 0.1-0.3 ppm three hours post treatment. In this enclosure having a volume of ~270 liters, 1.6 g NaDCC dihydrate should theoretically represent 5.9 ppm or ~3.4 ppm of available chlorine, although none could be traced either in the once-a-day or in the twice a day treatment. In other words, the effect of the treatment on the cell density as well as the additional parameters could not be explained merely by direct toxic effects of the compound.

Moreover, as stated before, this enclosure was positioned ~20 m away from a strong aerator that blended daily the ponds' water, and probably mixed pond-water with the water in the enclosure whether by spraying water from above or by pushing water through the open end of the enclosures from below. The correlation of all parameters (chlorophyll-a concentration on surface and at minus 50 cm, pH and DO (FIGS. 3A-D) independently in all 3 blocks of the trial clearly demonstrate that the treatment with a floating formulation comprising minute sub-concentrations of hypochlorous acid can cause a complete collapse of the harmful cyanobacterial population and potentially make way for other competing, opportunistic microorganisms.

Example 6

Use of the Floating Formulation to Reduce Cyanobacterial Cell Density [II]

Figure 4:
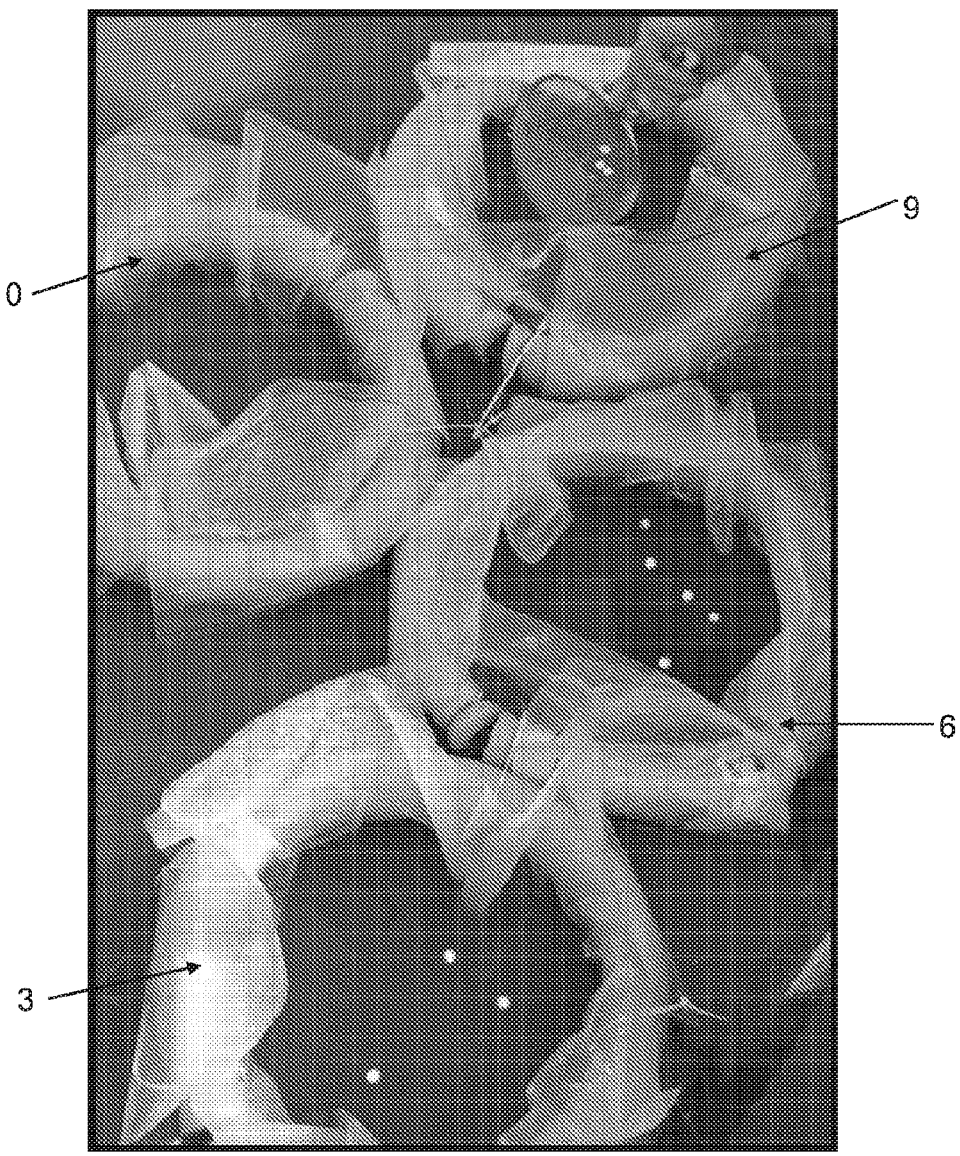
FIG. 4 shows images of exemplary enclosures without treatment treated with three capsules treated with 6 capsules and treated with 9 capsules.

In another experiment, enclosures (composed of a 40 cm long clear polyethylene tube) were set in an aerated shallow (30-100 cm deep) fish pond (G16 pond, Auburn University, Auburn, Ala., USA) which was heavily infested with the cyanobacterium *Oscillatoria* sp. with an initial cell density of ~$10^6$ filaments/ml. The enclosures were placed in the water while being open to both the water surface and the pond's floor. The following treatments were applied: (1) control with no treatment, (2) treatment with 3 capsules of a floating NaDCC formulation (3) treatment with 6 capsules of a floating NaDCC formulation, and (4) treatment with 9 capsules of a floating NaDCC formulation (see FIG. 4 showing exemplary enclosures). Each capsule contained 200 mg NaDCC dihydrate as the active compound in a floating formulation as described in Example 4. Treatments were applied at 19:00 at day 1, then at 8:00 AM on day 2, followed by a third and a last treatment at noon of the same day.

Figure 5:
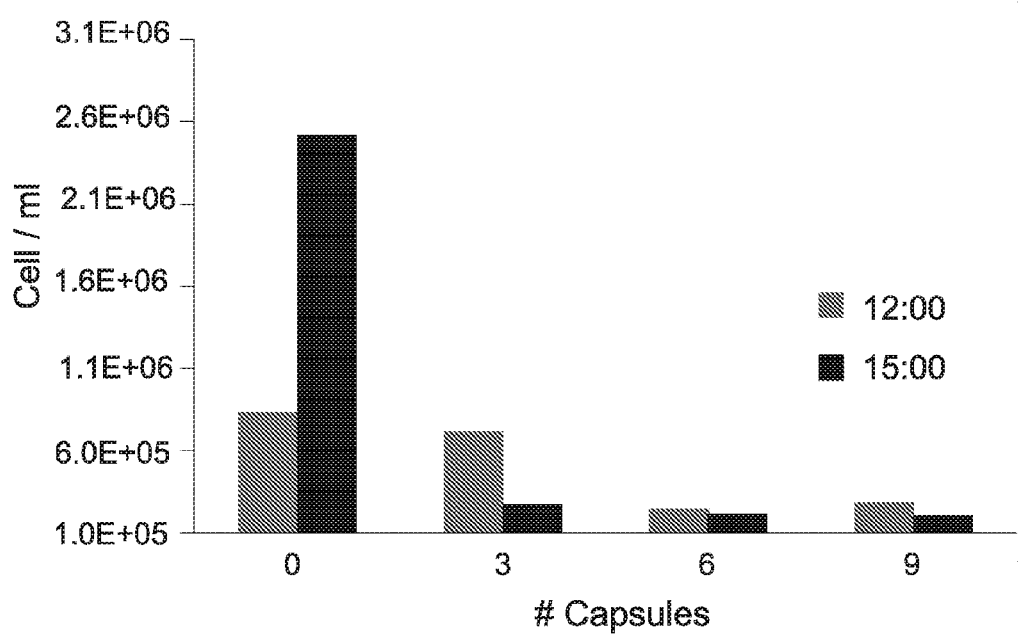
FIG. 5 is a graph showing the concentration of cyanobacterial cells/ml in enclosures treated with 3, 6 or 9 capsules, or without treatment (0), at two time points (at 12:00 and at 15:00).
Figure 6A:
FIG. 6 shows images of the water surface of an enclosure (A) no treatment, (B) treatment with 6 capsules.
Figure 6B:
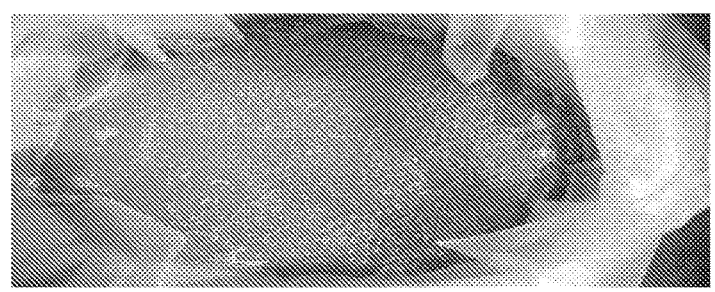
Figure 7:
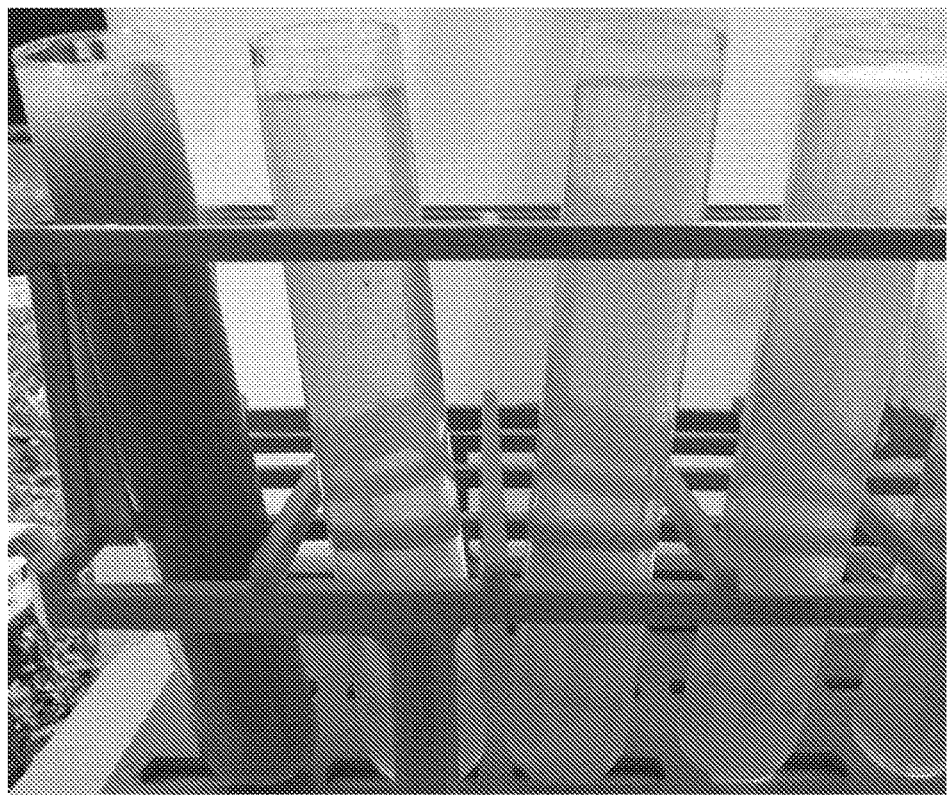
FIG. 7 shows images of vials containing water taken from the surface of the enclosures after treatment with two doses of capsules. Left vial—no treatment, subsequent vials from left to right 3, 6, and 9 capsules respectively.

Six capsules (total of 1.2 g NaDCC dihydrate as indicated above) successfully removed the entire scum in the enclosure (FIGS. 5 and 6). This was also exemplified with vials that were filled with the enclosures' water surface to demonstrate the relative turbidity across the treatments (FIG. 7). Cell numbers in the water surface dropped dramatically (one order of magnitude) during the treatment course. The pH on the surface decreased from pH 9.5 to pH 8 suggesting a decrease in photosynthesis activity. Total chlorine measurement was performed using a tracer device (Pocket Tracer code 1740, LaMotte, USA) to reveal at the end of the treatment total chlorine concentrations of 0.3 ppm chlorine at the 3-capsule treatment, 0.43 ppm chlorine at the 6-capsules treatment, and 1.22 ppm at the 9-capsules treatment (which were much lower than the theoretical expected concentrations of 8, 16 and 24 ppm, respectively, for a volume of 43 liters).

Example 7

Defining the Effect of Sodium Dichloroisocyanurate (NaDCC) Anhydrous on Variety of Hazardous Water Borne Insects Household bleach of 3% concentration did not harm the eggs of *Anopheles stevensi*, although at moderate chlorine concentrations larvae of many types of insects hatched earlier than non-treated controls. The early hatching altered their development and prevented them from transforming into adults.

The series of experiments presented below demonstrates, on different types of water-borne insects, that a relatively high concentration of bleach is required to destroy the insects' eggs.

a. *Culex quinquefasciatus* (*C. quinquefasciatus*)

Mosquito eggs were obtained from the Center for Disease control in Fort Collins, Colo. The eggs were counted and transferred to spot plates containing 8 ml of NaDCC anhydrous solution at 0, 50, 500, 5000, and 50,000 ppm. Each treatment concentration and control (0 ppm) was replicated 3 times within the same spot plate and transferred to an incubator set for 30° C. and 12 hrs of light and dark alterations for 25 hours Immediately, after transferring the eggs into the water many larvae within the control started to hatch and began swimming. Larvae were counted as living, hatched dead, or unhatched dead 25 hrs after the bioassay was initiated. Larvae were only counted as hatched if they were completely free from their egg casing. Data were analyzed by probit analysis with the PROBIT Procedure in SAS (Version 9.2, Cary N.C.), producing an $LC_{95}$ and natural response rate. The $LC_{95}$ for *C. quinquefasciatus* was 93.8 ppm. Egg shells were dissolved and unperceivable in the 50,000 ppm treatment, and mostly dissolved in the 5000 ppm treatment; larvae still maintained a shape suggesting that they never hatched.

b. *Anopheles stevensi*

*Anopheles stevensi* eggs were obtained from the collection of Insectary Core Facility and Parasite Culture at New York University School of Medicine. 60 eggs were counted and transferred to spot plates containing 8 ml of NaDCC anhydrous solution at 0, 0.58, 5.8, 58, 580 and 5800 ppm. Each treatment and control was replicated twice within the same spot plate and transferred to an incubator set for 30° C. and 12 hrs of light and dark alterations for 72 hours. Data were analyzed by probit analysis with the PROBIT Procedure in SAS (Version 9.2, Cary N.C.). Larvae were counted living, hatched dead, or unhatched dead 72 hrs after the bioassay was initiated. Individuals were only counted as hatched if they were completely free from their egg casing. The $LC_{95}$, for *Anopheles stevensi* was 270 ppm.

c. *Aedes aegypti*

*A. aegypti* eggs were obtained from the Center for Disease control in Fort Collins, Colo. The eggs were counted and transferred to spot plate treatment or control wells, and placed in an incubator. Larvae were counted as living, hatched dead, or unhatched dead 72 hours after the bioassay was initiated. Larvae were only counted as hatched if they were completely free from their egg casing. Data were analyzed by probit analysis with the PROBIT Procedure in SAS (Version 9.2, Cary N.C.), producing an $LC_{95}$ and natural response rate. The $LC_{95}$ for *A. aegypti* was 470 ppm. Egg shells were dissolved and unperceivable in the 50,000 ppm treatment, and mostly dissolved in the 5000 ppm treatment; larvae still maintained a shape suggesting that they never hatched.

d. Chironomidae

Non-biting midge eggs (Chironomidae: Tanypodinae) were obtained from the pond at Town Park, Auburn, Ala. The eggs were counted and transferred to spot plates containing 8 ml of NaDCC anhydrous solution at 0, 50, 500, 5000, and 50,000 ppm. Each treatment and control was replicated 3 times within the same spot plate and transferred to an incubator set for 30° C. and 12 hours of light and dark alterations for a week. Data were analyzed by probit analysis with the PROBIT Procedure in SAS (Version 9.2, Cary N.C.). Larvae were only counted as hatched if they were completely free from their egg casing. The $LC_{95}$, for Tanypodinae was 205.7 ppm, with an estimated natural mortality rate of 2.8%.

The invention claimed is:

1. A buoyant slow-release composition for locally targeting a floating photosynthetic microorganism bloom in an aquatic system, the buoyant composition comprising a photosynthetic microorganism inhibitor, a binding agent, at least one swelling agent and a solid floating agent,
    wherein the solid floating agent is selected from the group consisting of cellulose derivatives, ground plant biomass, saturated hydrocarbons, resinous materials, foam, wax and natural or synthetic latex;
    wherein the photosynthetic microorganism inhibitor comprises an oxidizing agent;
    wherein a concentration of said photosynthetic microorganism inhibitor is between 0.005 $g/m^2$ and about 50 $g/m^2$ of the surface of said aquatic system;
    wherein a concentration of said oxidizing agent is between 0.5 ppm to 50 ppm;
    wherein said composition is adapted to locally release said inhibitor into water in said system to contact and oxidize said bloom; and wherein said buoyant slow-release composition is adapted to move together with said bloom in said aquatic system.

2. The composition of claim 1, wherein said photosynthetic microorganism inhibitor is a water disinfectant.

3. The composition of claim 2, wherein the water disinfectant is selected from the group consisting of a chlorine releasing agent, a bromine-releasing agent, a peroxide-based compound, a copper salt, an aluminum salt, and combinations thereof.

4. The composition of claim 3, wherein the water disinfectant is calcium hypochlorite or sodium dichloroisocyanurate (NaDCC).

5. The composition of claim 4, wherein the solid floating agent is selected from wood dust, paraffin, rosin, extruded or expanded polystyrene foam silicone foam and wax.

6. The composition of claim 4, wherein the composition is in the form of particles, granules, flakes, powder, pellets, pills or a solution.

7. The composition of claim 1, wherein said photosynthetic microorganism bloom is selected from the group consisting of cyanobacterial growth, algal growth, microbial growth and plankton growth.

8. The composition of claim 1, comprising said photosynthetic microorganism inhibitor (0-40% w/w), said binding agent (0-12% w/w,) said at least one swelling agent (0-8%) and said solid floating agent (0-45%).

9. A method for locally targeting a surface-inhabiting photosynthetic microorganism bloom in an aquatic system, the method comprising:
    a. providing a buoyant slow-release composition according to claim 1; and
    b. applying said buoyant composition only locally in a vicinity of said bloom at a surface of said aquatic system thereby enabling said composition to contact said bloom without diffusing throughout an entire body of said aquatic system, thereby inducing at least a 50% reduction in said photosynthetic microorganism within a period of time in said aquatic system without leaving any detectable residue of said inhibitor; wherein said buoyant slow-release composition moves together with said bloom in said aquatic system.

10. The method of claim 8, wherein said at least one photosynthetic microorganism inhibitor comprises an oxidizing water disinfectant.

11. The method of claim 10, wherein said water disinfectant is selected from the group consisting of a chlorine releasing agent, a bromine-releasing agent, a peroxide-based compound, a copper salt, an aluminum salt, and any combination thereof.

12. The method of claim 10, wherein the water disinfectant is calcium hypochlorite or sodium dichloroisocyanurate (NaDCC).

13. The method of claim 9, wherein the composition is in the form of particles, granules, flakes, a powder, pellets, pills, a solution or a combination thereof.

14. A method according to claim 9, wherein said at least one photosynthetic microorganism is selected from the group consisting of a cyanobacterium, an alga, a plankton and combinations thereof.

15. A method according to claim 9, wherein the applying step follows detection of the bloom in the aquatic system.

16. The method of claim 9, wherein the applying step is performed at a beginning of a seasonal bloom.

17. A method according to claim 9, wherein said period of time is three hours.

18. A method according to claim 9, wherein said period of time is at least three days and said at least a 50% reduction is at least a 99% reduction.

19. A method according to claim 9, wherein said photosynthetic microorganism is a cyanobacterium wherein said composition is applied to said surface at a concentration of between about 0.005 g/m$^2$ and about 50 g/m$^2$, or between about 0.5 ppm and about 50 ppm of said inhibitor agent.

20. The method of claim 19, wherein said applying step is repeated after a several hour interval.

21. The method of claim 19, wherein said applying step is performed three times a day, or twice a day, or once a day, or once a week, or once every two weeks, or once every three weeks, or once a month or at longer intervals.

22. The method of claim 8, wherein the applying step is performed by manual or mechanical dusters, or by spreading a liquid solution from a boat or a plane.

* * * * *